(12) United States Patent
Beaudoin et al.

(10) Patent No.: US 7,537,215 B2
(45) Date of Patent: May 26, 2009

(54) METHOD AND APPARATUS FOR SECURING STRETCHABLE FILM USING VACUUM

(75) Inventors: Harold A. Beaudoin, Sheboygan Falls, WI (US); Wayne S. Lutzke, Plymouth, WI (US); Hubert P. Van de Pas, Plymouth, WI (US)

(73) Assignee: Curt G. Joa, inc., Sheboygan Falls, WI (US)

( * ) Notice: Subject to any disclaimer, the term of this patent is extended or adjusted under 35 U.S.C. 154(b) by 553 days.

(21) Appl. No.: 11/112,160

(22) Filed: Apr. 22, 2005

(65) Prior Publication Data

US 2005/0275148 A1    Dec. 15, 2005

Related U.S. Application Data

(60) Provisional application No. 60/579,804, filed on Jun. 15, 2004.

(51) Int. Cl.
*B65H 5/02* (2006.01)
(52) U.S. Cl. .................. 271/276; 271/196; 156/164
(58) Field of Classification Search .............. 271/276, 271/196; 156/164
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,605,842 A | 11/1926 | Jones | |
| 1,686,595 A | * 10/1928 | Belluche | ............... 271/107 |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |

(Continued)

FOREIGN PATENT DOCUMENTS

BE    1007854    11/1995

(Continued)

OTHER PUBLICATIONS

Reciprocating Mechanisms, Ingenious Mechanisms for Designers and Inventors, Franklin Jones vol. 1.

*Primary Examiner*—Patrick H Mackey
*Assistant Examiner*—Luis Gonzalez
(74) *Attorney, Agent, or Firm*—Ryan Kromholz & Manion S.C.

(57) ABSTRACT

A vacuum wheel for securing and retaining various sizes of stretchable film is disclosed. The outer surface of the vacuum wheel includes an advantageous pattern of vacuum openings and vacuum slots, wherein the vacuum slots provide vacuum communication between at least two of the vacuum openings. A preferred embodiment provides a chevron or zig-zag shaped pattern of vacuum openings and vacuum slots configured to provide improved vacuum holding strength.

4 Claims, 8 Drawing Sheets

U.S. PATENT DOCUMENTS

| | | |
|---|---|---|
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |

| | | | | | | |
|---|---|---|---|---|---|---|
| 4,642,150 A * | 2/1987 | Stemmler ............... 156/164 | | 5,415,649 A | 5/1995 | Watanabe et al. |
| 4,642,839 A | 2/1987 | Urban | | 5,421,924 A | 6/1995 | Ziegelhoffer et al. |
| 4,650,530 A | 3/1987 | Mahoney et al. | | 5,424,025 A | 6/1995 | Hanschen et al. |
| 4,663,220 A | 5/1987 | Wisneski et al. | | 5,429,576 A | 7/1995 | Doderer-Winkler |
| 4,672,705 A | 6/1987 | Bors et al. | | 5,435,802 A | 7/1995 | Kober |
| 4,675,062 A | 6/1987 | Instance | | 5,449,353 A | 9/1995 | Watanabe et al. |
| 4,693,056 A | 9/1987 | Raszewski | | 5,464,401 A | 11/1995 | Hasse et al. |
| 4,701,239 A | 10/1987 | Craig | | 5,486,253 A | 1/1996 | Otruba |
| 4,723,698 A | 2/1988 | Schoonderbeek | | 5,494,622 A | 2/1996 | Heath et al. |
| 4,726,874 A | 2/1988 | Van Vilet | | 5,531,850 A | 7/1996 | Herrmann |
| 4,726,876 A | 2/1988 | Tomsovic | | 5,540,647 A | 7/1996 | Weiermann et al. |
| 4,743,241 A | 5/1988 | Igaue et al. | | 5,545,275 A | 8/1996 | Herrin et al. |
| 4,751,997 A | 6/1988 | Hirsch | | 5,545,285 A * | 8/1996 | Johnson ............... 156/496 |
| 4,753,429 A | 6/1988 | Irvine et al. | | 5,552,013 A | 9/1996 | Ehlert et al. |
| 4,756,141 A | 7/1988 | Hirsch et al. | | 5,556,360 A | 9/1996 | Kober et al. |
| 4,764,325 A | 8/1988 | Angstadt | | 5,556,504 A | 9/1996 | Rajala et al. |
| 4,765,780 A | 8/1988 | Angstadt | | 5,560,793 A | 10/1996 | Ruscher et al. |
| 4,776,920 A | 10/1988 | Ryan | | 5,602,747 A | 2/1997 | Rajala |
| 4,777,513 A | 10/1988 | Nelson | | 5,624,420 A | 4/1997 | Bridges et al. |
| 4,782,647 A | 11/1988 | Williams et al. | | 5,624,428 A | 4/1997 | Sauer |
| 4,785,986 A | 11/1988 | Daane et al. | | 5,628,738 A | 5/1997 | Suekane |
| 4,795,510 A | 1/1989 | Wittrock et al. | | 5,634,917 A | 6/1997 | Fujioka et al. |
| 4,798,353 A | 1/1989 | Peugh | | 5,643,165 A | 7/1997 | Klekamp |
| 4,801,345 A | 1/1989 | Dussaud et al. | | 5,643,396 A | 7/1997 | Rajala et al. |
| 4,802,570 A | 2/1989 | Hirsch et al. | | 5,645,543 A | 7/1997 | Nomura et al. |
| 4,840,609 A | 6/1989 | Jones et al. | | 5,659,229 A | 8/1997 | Rajala |
| 4,845,964 A | 7/1989 | Bors et al. | | 5,660,657 A | 8/1997 | Rajala et al. |
| 4,864,802 A | 9/1989 | D'Angelo | | 5,660,665 A | 8/1997 | Jalonen |
| 4,880,102 A | 11/1989 | Indrebo | | 5,683,376 A | 11/1997 | Kato et al. |
| 4,888,231 A | 12/1989 | Angstadt | | RE35,687 E | 12/1997 | Igaue et al. |
| 4,892,536 A | 1/1990 | DesMarais et al. | | 5,693,165 A | 12/1997 | Schmitz |
| 4,904,440 A | 2/1990 | Angstadt | | 5,699,653 A | 12/1997 | Hartman et al. |
| 4,908,175 A | 3/1990 | Angstadt | | 5,707,470 A | 1/1998 | Rajala et al. |
| 4,909,019 A | 3/1990 | Delacretaz et al. | | 5,711,832 A | 1/1998 | Glaug et al. |
| 4,925,520 A | 5/1990 | Beaudoin et al. | | 5,725,518 A | 3/1998 | Coates |
| 4,927,322 A | 5/1990 | Schweizer et al. | | 5,745,922 A | 5/1998 | Rajala et al. |
| 4,927,582 A | 5/1990 | Bryson | | 5,746,869 A | 5/1998 | Hayden et al. |
| 4,937,887 A | 7/1990 | Schreiner | | 5,749,989 A | 5/1998 | Linman et al. |
| 4,963,072 A | 10/1990 | Miley et al. | | 5,788,797 A | 8/1998 | Herrin et al. |
| 4,987,940 A | 1/1991 | Straub et al. | | 5,817,199 A | 10/1998 | Brennecke et al. |
| 4,994,010 A | 2/1991 | Doderer-Winkler | | 5,829,164 A | 11/1998 | Kotitschke |
| 5,000,806 A | 3/1991 | Merkatoris et al. | | 5,836,931 A | 11/1998 | Toyoda et al. |
| 5,021,111 A | 6/1991 | Swenson | | 5,858,012 A | 1/1999 | Yamaki et al. |
| 5,025,910 A | 6/1991 | Lasure et al. | | 5,865,393 A | 2/1999 | Kreft et al. |
| 5,045,039 A | 9/1991 | Bay | | 5,868,727 A | 2/1999 | Barr et al. |
| 5,062,597 A | 11/1991 | Martin et al. | | 5,876,027 A | 3/1999 | Fukui et al. |
| 5,064,179 A | 11/1991 | Martin | | 5,876,792 A | 3/1999 | Caldwell |
| 5,080,741 A | 1/1992 | Nomura et al. | | 5,879,500 A | 3/1999 | Herrin et al. |
| 5,094,658 A | 3/1992 | Smithe et al. | | 5,902,431 A | 5/1999 | Wilkinson et al. |
| 5,096,532 A | 3/1992 | Neuwirth et al. | | 5,932,039 A | 8/1999 | Popp et al. |
| 5,108,017 A | 4/1992 | Adamski et al. | | 5,938,193 A * | 8/1999 | Bluemle et al. ............... 271/243 |
| 5,109,767 A | 5/1992 | Nyfeler et al. | | 5,964,390 A | 10/1999 | B.o slashed.rresen et al. |
| 5,110,403 A | 5/1992 | Ehlert | | 5,964,970 A | 10/1999 | Woolwine et al. |
| 5,127,981 A | 7/1992 | Straub et al. | | 6,036,805 A | 3/2000 | McNichols |
| 5,131,525 A | 7/1992 | Musschoot | | 6,043,836 A * | 3/2000 | Kerr et al. ............... 347/262 |
| 5,147,487 A | 9/1992 | Nomura et al. | | 6,050,517 A | 4/2000 | Dobrescu et al. |
| 5,163,594 A | 11/1992 | Meyer | | 6,074,110 A | 6/2000 | Verlinden et al. |
| 5,171,239 A | 12/1992 | Igaue et al. | | 6,076,442 A | 6/2000 | Arterburn et al. |
| 5,176,244 A | 1/1993 | Radzins et al. | | 6,098,249 A | 8/2000 | Toney et al. |
| 5,183,252 A * | 2/1993 | Wolber et al. ............... 271/276 | | 6,123,792 A | 9/2000 | Samida et al. |
| 5,188,627 A | 2/1993 | Igaue et al. | | 6,183,576 B1 | 2/2001 | Couillard et al. |
| 5,195,684 A | 3/1993 | Radzins et al. | | 6,210,386 B1 | 4/2001 | Inoue |
| 5,203,043 A | 4/1993 | Riedel | | 6,212,859 B1 | 4/2001 | Bielik, Jr. et al. |
| 5,213,645 A | 5/1993 | Nomura et al. | | 6,250,048 B1 | 6/2001 | Linkiewicz |
| 5,223,069 A | 6/1993 | Tokuno et al. | | 6,264,784 B1 | 7/2001 | Menard et al. |
| 5,226,992 A | 7/1993 | Morman | | 6,276,421 B1* | 8/2001 | Valenti et al. ............... 156/521 |
| 5,246,433 A | 9/1993 | Hasse et al. | | 6,276,587 B1 | 8/2001 | Borresen et al. |
| 5,267,933 A | 12/1993 | Precoma | | 6,306,122 B1 | 10/2001 | Narawa et al. |
| 5,308,345 A | 5/1994 | Herrin | | 6,309,336 B1 | 10/2001 | Muessig et al. |
| 5,328,438 A | 7/1994 | Crowley | | 6,312,420 B1 | 11/2001 | Sasaki et al. |
| 5,340,424 A | 8/1994 | Matsushita | | 6,314,333 B1 | 11/2001 | Rajala et al. |
| 5,368,893 A | 11/1994 | Sommer et al. | | 6,315,022 B1 | 11/2001 | Herrin et al. |
| 5,407,513 A | 4/1995 | Hayden et al. | | 6,336,921 B1 | 1/2002 | Kato et al. |

| | | |
|---|---|---|
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Gloug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1 | 2/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,572,520 B2 | 6/2003 | Blumle |
| 6,581,517 B1 * | 6/2003 | Becker et al. ............ 101/389.1 |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,684,925 B2 | 2/2004 | Nagate et al. |
| 6,766,817 B2 | 7/2004 | da Silva |
| D497,991 S | 11/2004 | Otsubo et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,918,404 B2 | 7/2005 | Dias da Silva |
| 6,978,486 B2 | 12/2005 | Zhou et al. |
| 7,066,586 B2 | 6/2006 | da Silva |
| 7,077,393 B2 | 7/2006 | Ishida |
| 7,172,666 B2 | 2/2007 | Groves et al. |
| 7,214,174 B2 | 5/2007 | Allen et al. |
| 7,247,219 B2 | 7/2007 | O'Dowd |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2002/0096241 A1 | 7/2002 | Instance |
| 2003/0000620 A1 | 1/2003 | Herrin et al. |
| 2003/0015209 A1 | 1/2003 | Gingras et al. |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0112517 A1 | 6/2004 | Groves et al. |
| 2004/0164482 A1 * | 8/2004 | Edinger ..................... 271/197 |
| 2005/0000628 A1 | 1/2005 | Norrley |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |

FOREIGN PATENT DOCUMENTS

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| DE | 102006047280 | 4/2007 |
| EP | 0044206 | 1/1982 |
| EP | 0048011 | 3/1982 |
| EP | 0089106 | 9/1983 |
| EP | 0206208 | 12/1986 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 990588 | 4/2000 |
| EP | 1132325 | 9/2001 |
| EP | 1272347 | 1/2003 |
| EP | 1571249 | 9/2005 |
| EP | 1619008 | 1/2006 |
| EP | 1707168 | 4/2006 |
| ES | 509706 | 11/1982 |
| ES | 520559 | 12/1983 |
| ES | 296211 | 12/1987 |
| FR | 2255961 | 7/1975 |
| FR | 2891811 | 4/2007 |
| GB | 191101501 | 1/1912 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 439897 | 8/1990 |
| GB | 2288316 | 10/1995 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10035621 | 2/1998 |
| JP | 10-277091 | 10/1998 |
| SE | 0602047 | 5/2007 |
| WO | WO9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO2005075163 | 1/2005 |

* cited by examiner

METHOD AND APPARATUS FOR SECURING STRETCHABLE FILM USING VACUUM

RELATED APPLICATION

This application claims the benefit of U.S. Provisional Patent Application Ser. No. 60/579,804, filed 15 Jun. 2004, and entitled "Method and Apparatus for Securing Stretchable Film Using Vacuum."

BACKGROUND OF THE INVENTION

This invention relates to the art of vacuum wheels and more particularly to a vacuum wheel vacuum opening configuration that has improved vacuum holding power to hold articles in place.

A vacuum wheel in the form of a rotary member having vacuum holes opening onto a cylindrical outer surface for the support and retention of stretchable film is typically a component of an apparatus that is known for various applications. A common example where an apparatus including a vacuum wheel would be used includes the construction of apparel that is worn on the body such as disposable diapers. In this application, an elastic waistband is stretched before being inserted into the waistband region. An example of such an apparatus is described in U.S. Pat. No. 4,925,520, commonly owned by the assignee hereof.

It is a common problem in such devices to experience insufficient vacuum holding strength for the materials to be held in place in relation to the shear forces applied to the materials. Another problem, where vacuum slots are used to improve the vacuum holding strength, is the loss of vacuum pressure along an edge of the vacuum slot. The vacuum holding force is a function of the area under the vacuum and the edges of the vacuum openings and slots against which the forces are applied. Simple round holes must be kept small in diameter to prevent the film from being sucked deep into the vacuum openings. The small area limits the holding force, and the small size limits the working edge length.

Various approaches have been taken for retaining flexible materials on a vacuum wheel. One approach has been to increase the number of vacuum openings on the available surface of the vacuum wheel. This can cause the size of the vacuum wheel to exceed possible size requirements for use in an apparatus. Another approach has been to include mechanical gripping means to engage the ends of the film to be stretched, such as pins or other rough surface features, in addition to the vacuum or drawing force on the article to be stretched. Although this approach improves the gripping of the article to the vacuum wheel, it does not allow the article to slip over the vacuum wheel when the shear force applied to the article exceeds the vacuum holding strength.

Because of the foregoing deficiencies in the art, an object of the present invention is to provide a compact vacuum wheel configuration that solves these problems by making the available vacuum wheel surface area more effective by improving its vacuum holding strength.

SUMMARY OF THE INVENTION

In general terms, this new apparatus comprises a vacuum wheel with a vacuum opening configuration that provides improved holding strength. This is an improved apparatus for holding elastic film on a surface using vacuum. Specifically, one aspect of the improvement lies in the configuration of the vacuum opening pattern and the matter in which it "bites" into the film.

It has been found that the film-holding strength of a vacuum is strongly related to the shape and direction of the vacuum pattern. Designing the pattern to give a favorable orientation relative to the force applied can optimize the holding strength.

Slots are often used as methods of increasing edge length along a vacuum pattern, but they are subject to having their seal with the film broken completely if they leak at any point along their edge. Orienting the slots favorably relative to the lines of force can improve the holding power.

The subject invention is an expansion on the slot approach, but uses a multi-chevron or zig-zag pattern to improve the holding power. The chevron, or "W" pattern, provides increased holding area and increased edge length, but importantly, it provides for holding the film along several inside and outside corners, which tend to tighten, rather than loosen their grip when subject to high shear forces.

The invention provides a vacuum wheel with improved vacuum holding strength.

DESCRIPTION OF THE PREFERRED EMBODIMENT

Figure 1:
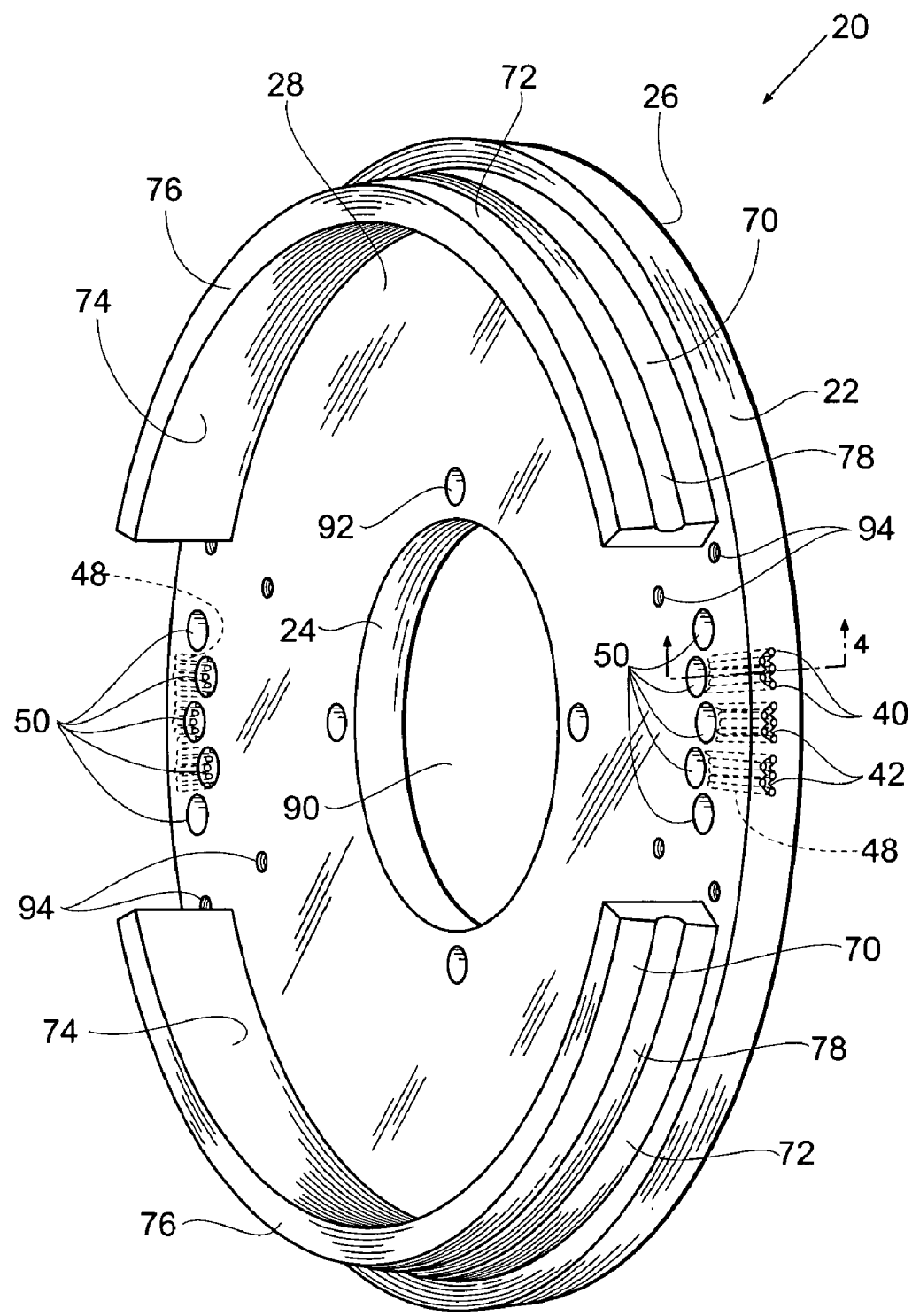
FIG. 1 is a perspective view of a vacuum wheel that embodies the present invention.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Referring to the drawings, wherein like numerals represent like parts throughout the views, there is generally designated at 20 a vacuum wheel for securing stretchable film according to the present invention. As seen particularly in FIGS. 1 and 2, the vacuum wheel 20 preferably includes a generally cylindrical outer surface 22, a cylindrical inner surface 24, a first side 26, and a second side 28.

Figure 3A:
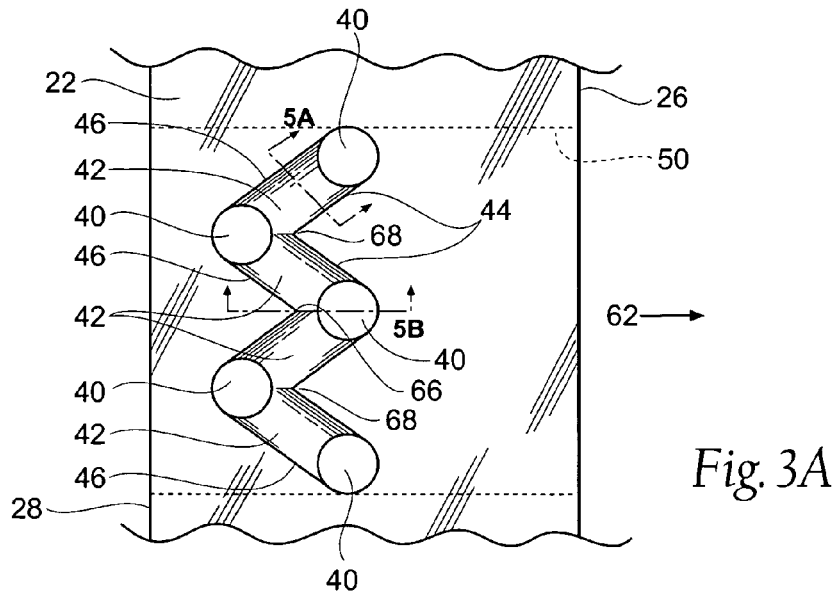
FIG. 3a is a perspective view of a chevron vacuum opening pattern embodied in the vacuum wheel shown in FIG. 1.
Figure 3B:
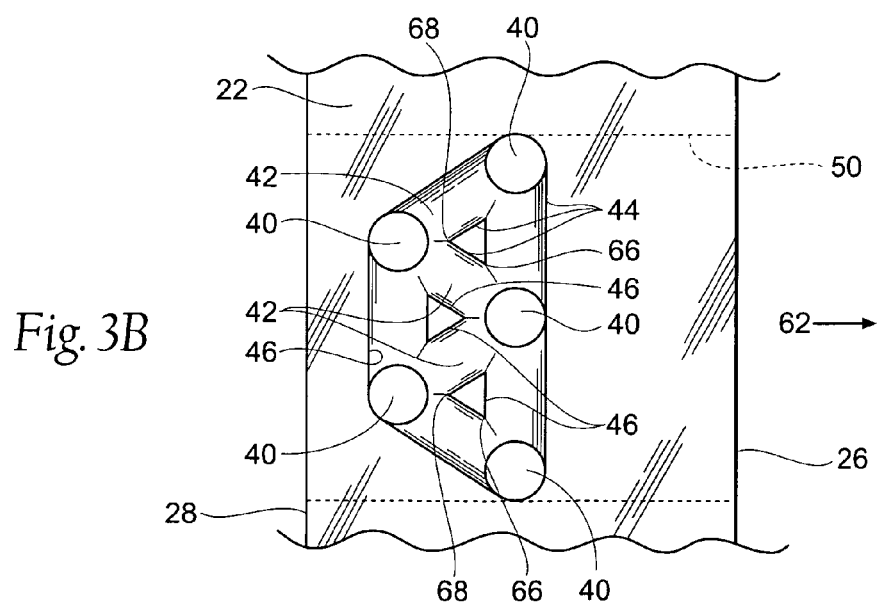
FIG. 3b is a perspective view of an alternative vacuum opening pattern embodied in the vacuum wheel shown in FIG. 1.

The cylindrical outer surface 22 includes a plurality of vacuum openings 40 spaced apart from each other through which vacuum is drawn. The vacuum openings 40 are preferably in vacuum contact with each other by way of vacuum slots 42, which are slots or grooves within the outer peripheral surface 22 of the vacuum wheel 20. These vacuum slots 42 may be milled or formed, and preferably provide vacuum contact between at least two vacuum openings 40. The vacuum slots 42 are adapted to have a first edge 44 and a second edge 46. In a preferred embodiment, the vacuum openings 40 and vacuum slots 42 define a chevron or zig-zag pattern (see FIG. 3*a*), although other advantageous patterns are within the scope of this invention (for example, FIG. 3*b*—also a chevron, but with additional slots).

Still referring to FIG. 1, it will be appreciated that for every one rotation of the vacuum wheel 20, two sets of vacuum openings 40 will have been rotated, allowing the ability to pick up product, such as stretchable film, with the vacuum twice per revolution.

Figure 4:
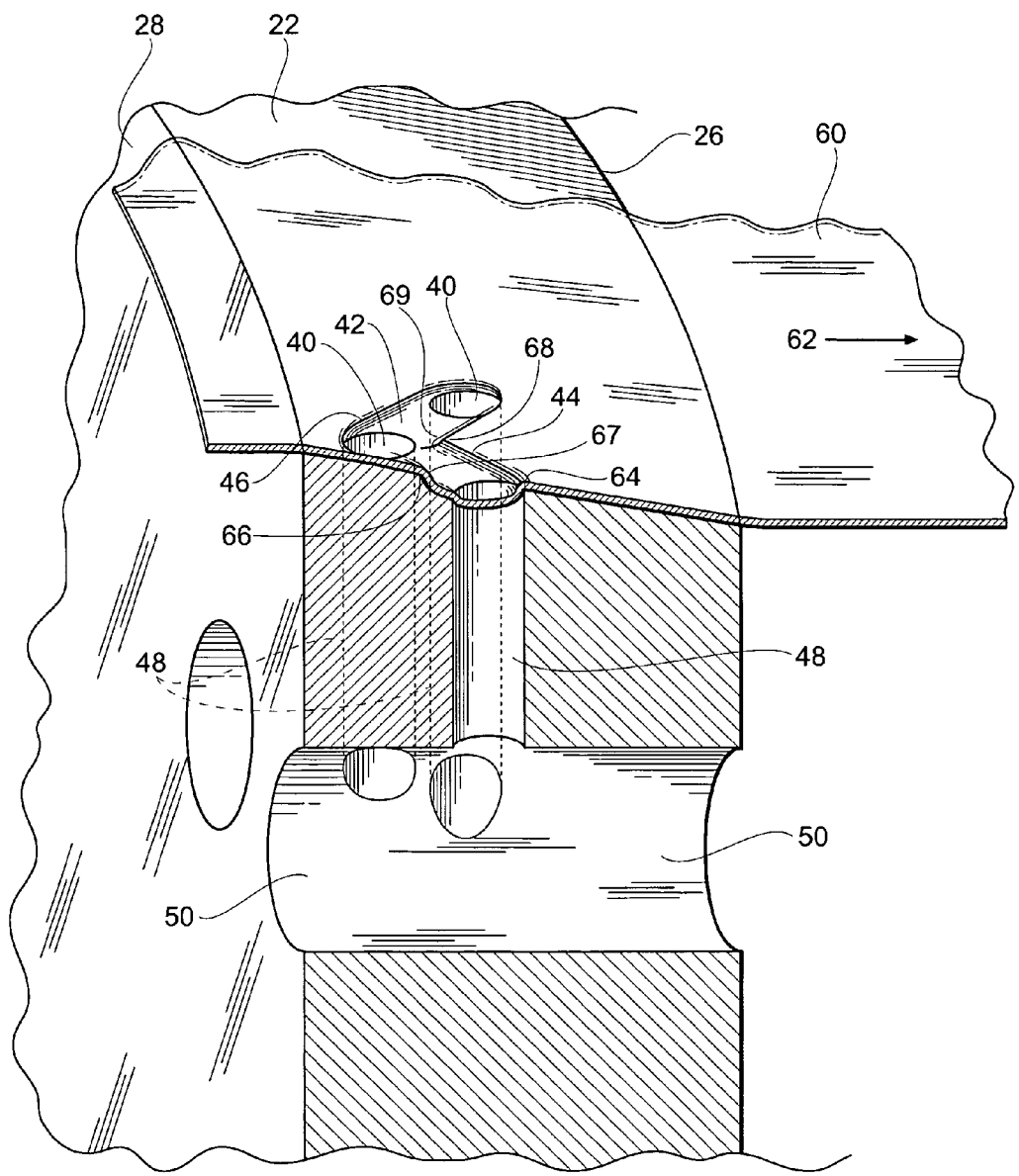
FIG. 4 is a fragmentary cross section view taken along line 4-4 of the vacuum wheel in FIG. 1 showing a direction of shear force applied to a segment of film and the resulting vacuum forces on the segment of film.

As best seen in FIG. 4, the vacuum openings 40 in conjunction with the vacuum slots 42 are adapted to attract and retain under the influence of vacuum a segment of film or other material 60. When a vacuum is applied to the vacuum wheel 20 (vacuum source not shown) and a segment of film 60 is placed over the vacuum openings 40 and vacuum slots 42, the vacuum will attract and retain the segment of film 60 on the outer surface 22 of the vacuum wheel 20. When a shear force is applied to the segment of film 60 in the direction indicated by arrow 62, the vacuum openings 40 and the first edge 44 of the vacuum slots 42 provide an area of retaining vacuum force 64 on the segment of film 60.

In addition to the retaining vacuum force 64, the advantageous vacuum opening 40 and vacuum slot 42 chevron pattern provides a number of inside 66 and outside 68 corners. These inside 66 and outside 68 corners create additional inside corner forces 67 and outside corner forces 69. The inside 67 and outside 69 corner forces provide increased holding area, and tend to tighten, rather than loosen their grip when subject to high shear forces. The chevron or zig-zag pattern of vacuum openings 40 and vacuum slots 42 seen in FIGS. 3*a* and 3*b* takes advantage of these vacuum retaining forces 64, 67, and 69 to hold the segment of film 60 in place, yet allows for the segment of film to slip over the vacuum openings 40 and vacuum slots 42 when the shear force applied to the segment of film 60 is stronger than the retaining vacuum forces 64, 67, and 69 on the segment of film 60.

Vacuum source is applied to wheel 20 by placing a fixed vacuum manifold assembly very close to surface 26 of wheel 20 (preferably 0.005"±0.002" gap). The inserts mounted to surface 28 of wheel 20 finish or close the vacuum communication, and may also include vacuum holes to communicate vacuum to additional elastic material contact surfaces.

Referring to FIG. 1, the vacuum wheel 20 axle or shaft mounting aperture 90 and cylindrical inner surface 24 of the vacuum wheel 20 can be seen. The axle mounting aperture 90, along with a plurality of bolt mounting apertures 92 provides the means for mounting the vacuum wheel 20 within an article transfer device or the like, such as that described in Ser. No. 09/695,961 [owned by the common assignee hereof]. The inner surface 24 of the vacuum wheel 20 has a central rotational axis that is disposed parallel to the outer surface 22 of the vacuum wheel 20.

The second side 28 of the vacuum wheel 20 preferably has a plurality of longitudinal vacuum ports 50 formed through it that may be parallel to but offset from an axis of rotation of the vacuum wheel 20. The vacuum ports 50 are preferably configured to connect to an external vacuum source (not shown). Extending generally radially outwardly from the vacuum ports 50 are vacuum passageways 48. Each vacuum passageway 48 extends from the vacuum port 50 to the vacuum opening 40 on the outer surface 22 of the vacuum wheel 20.

Figure 2:
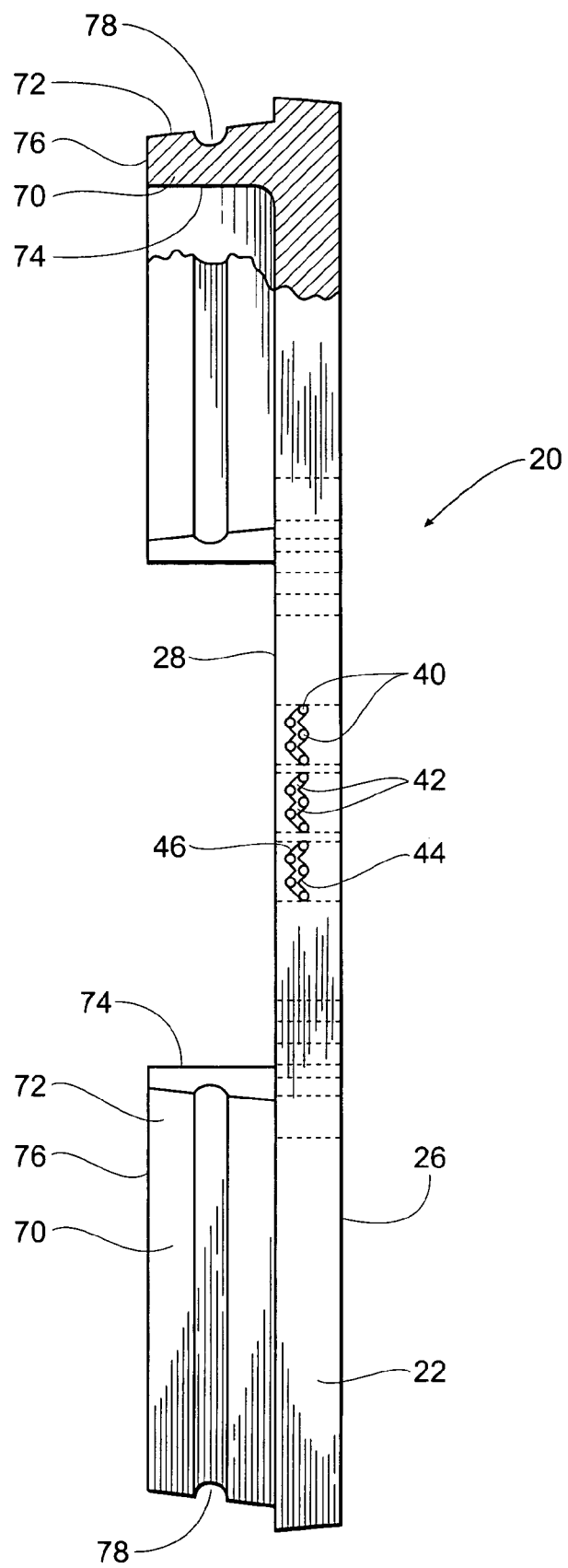
FIG. 2 is a side elevation view, with a partial section, of the vacuum wheel shown in FIG. 1.
Figure 7:
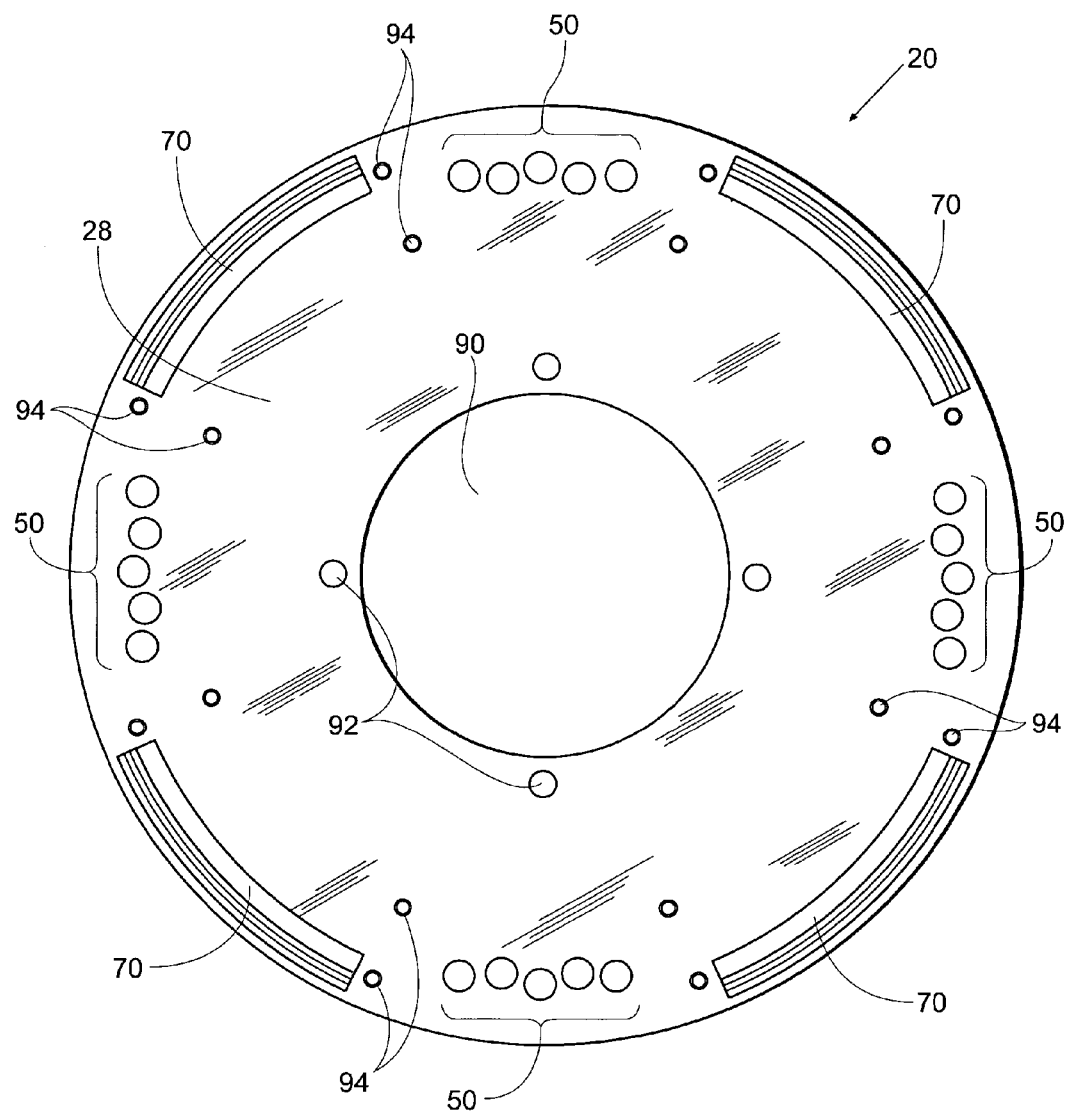
FIG. 7 is a side elevation view of an alternative vacuum wheel-with additional vacuum ports and protuberances.

Referring now to FIGS. 1 and 2, the vacuum wheel 20 preferably includes at least one protuberance 70 extending generally outwardly from the second side 28 of the vacuum wheel 20 and parallel to the outer surface 22, and ending at the protuberance 70 first side 76. The protuberances 70 include an outer surface 72 and an inner surface 74. In a preferred embodiment, disposed within the outer surface 72 of the protuberance 70 is a groove 78 formed therein. The protuberances 70 are arranged 180 degrees apart in this embodiment, but they may be separated by other angles in other designs. In some cases, more than one pair of protuberances are used. FIG. 7 shows such an alternative embodiment of the vacuum wheel 20 including four protuberances 70, although an odd number of protuberances 70 may be used as well.

The purpose of the groove 78 in the outer surface 72 of the protuberance 70 is for aligning/guiding a belt (not shown). The surface of the belt becomes a contact surface to the elastic material. Different types of belts can provide different contact (or gripping) surfaces, or different belt profiles can be used.

Preferably, there are 5 vacuum port holes per each grouping of 15 vacuum holes. Still preferably, 3 of these vacuum port holes are in vacuum communication with the 15 vacuum holes. The remaining two vacuum port holes are there in case the length of the elastic material patch requires more than the 15 shown vacuum holes. Additional "W" patterns of vacuum holes can be machined into the wheel, as needed.

The surface 22 of wheel 20 is a "holding" surface preferably. The actual transfer surface (bumping or laying the elastic material onto carrier web) is provided for by the inserts.

The wheels are preferably used in pairs (left and right or operator side and drive side). The wheels are canted / \ so at the transfer-on point the wheel outer surfaces are closer together than at the transfer-off point (180 degrees rotation). The elastic material patch transfers onto the wheels in an unstretched state, and transfers off the wheels in a stretched state. The angles on the outer surface of the wheels are there to keep the outer surfaces of the wheels parallel to the transfer surfaces.

Figure 5A:
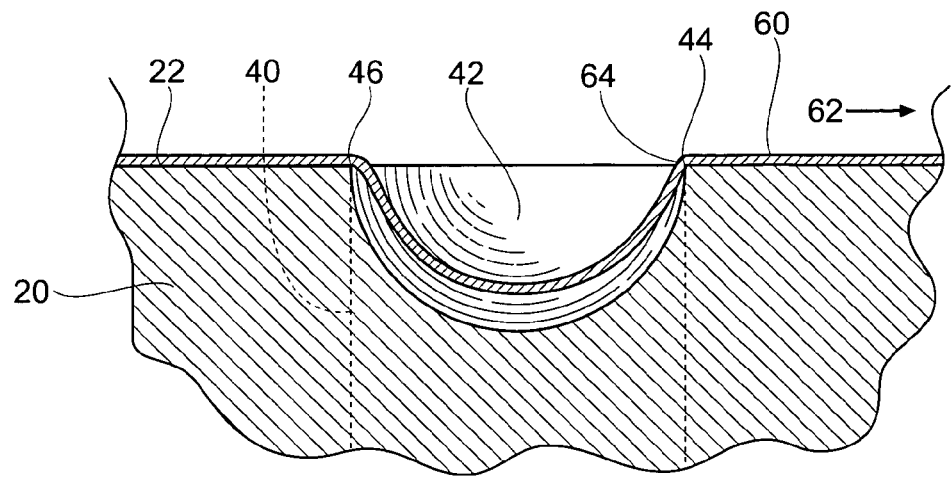
FIGS. 5A and 5B are a side elevation views, with portions cut away, of the vacuum wheel shown in FIG. 3A.
Figure 5B:
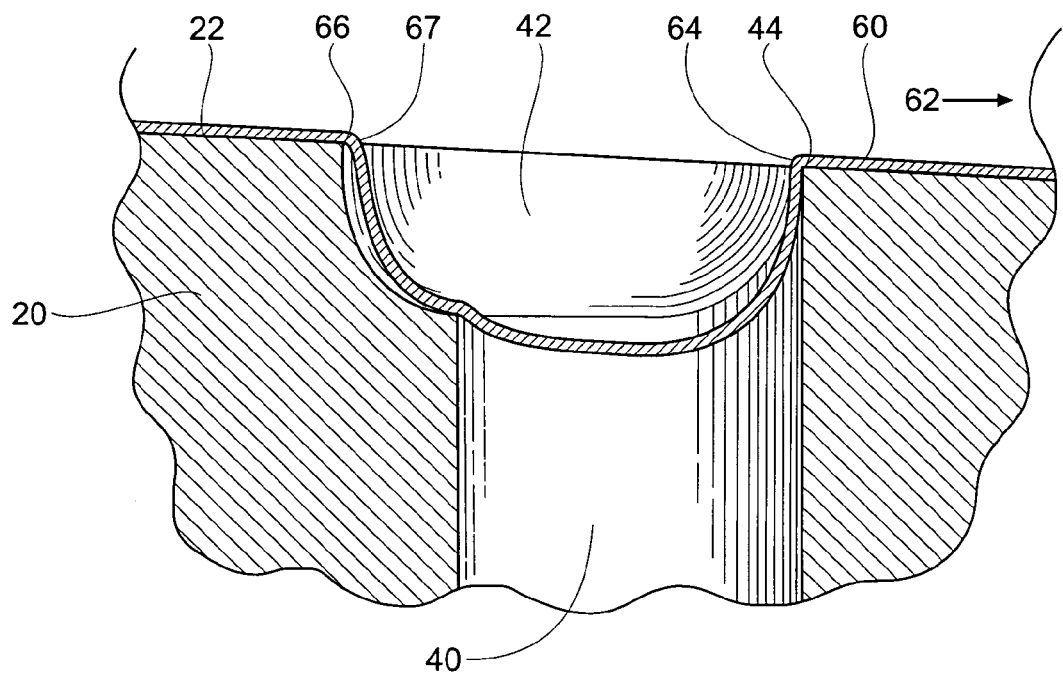
Figure 6:
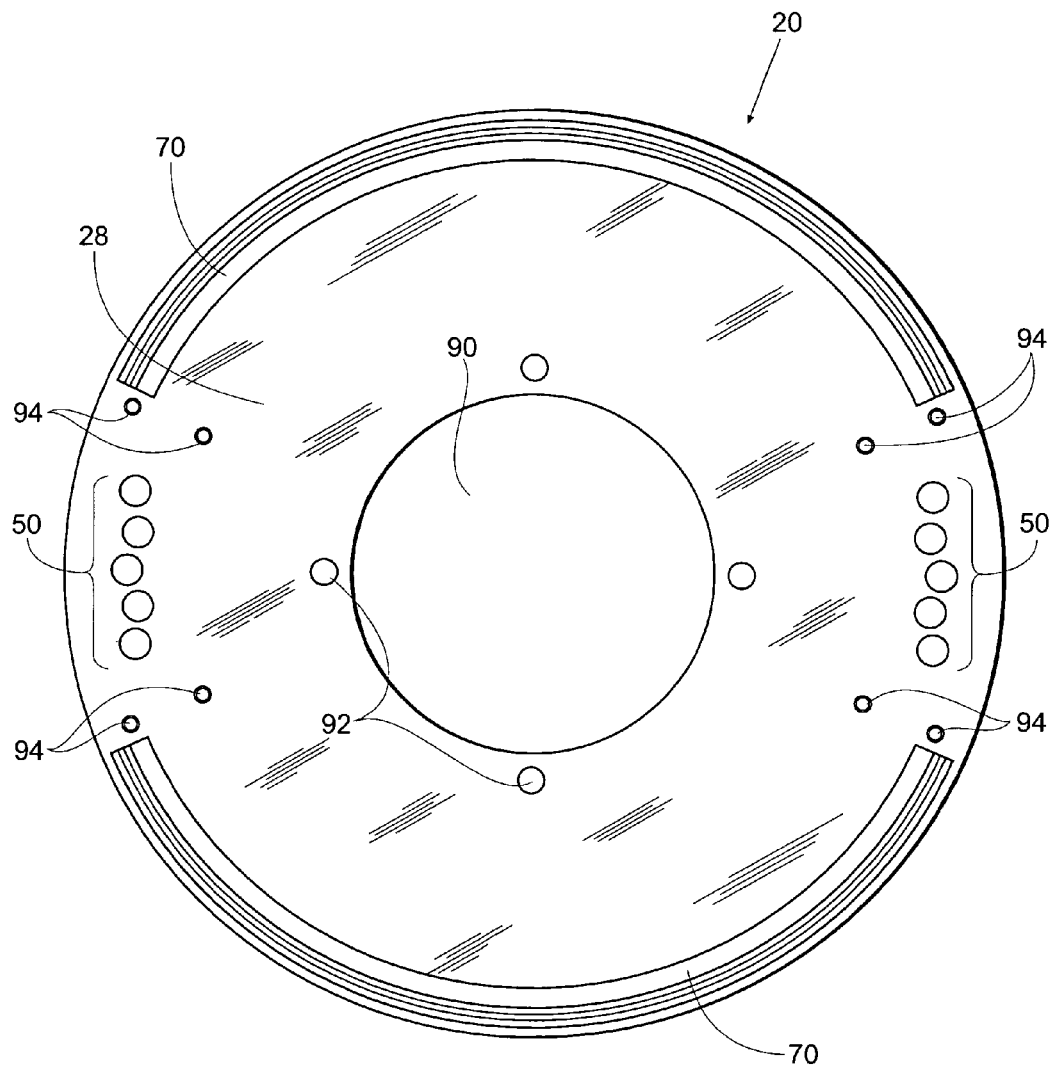
FIG. 6 is a side elevation view of an alternative vacuum wheel with additional vacuum ports and protuberances.

Referring to FIG. 6, in the alternative embodiment shown, the vacuum wheel 20 includes four sets of vacuum opening 40 patterns as compared to two sets of vacuum opening 40 patterns in FIG. 5.

Figure 8:
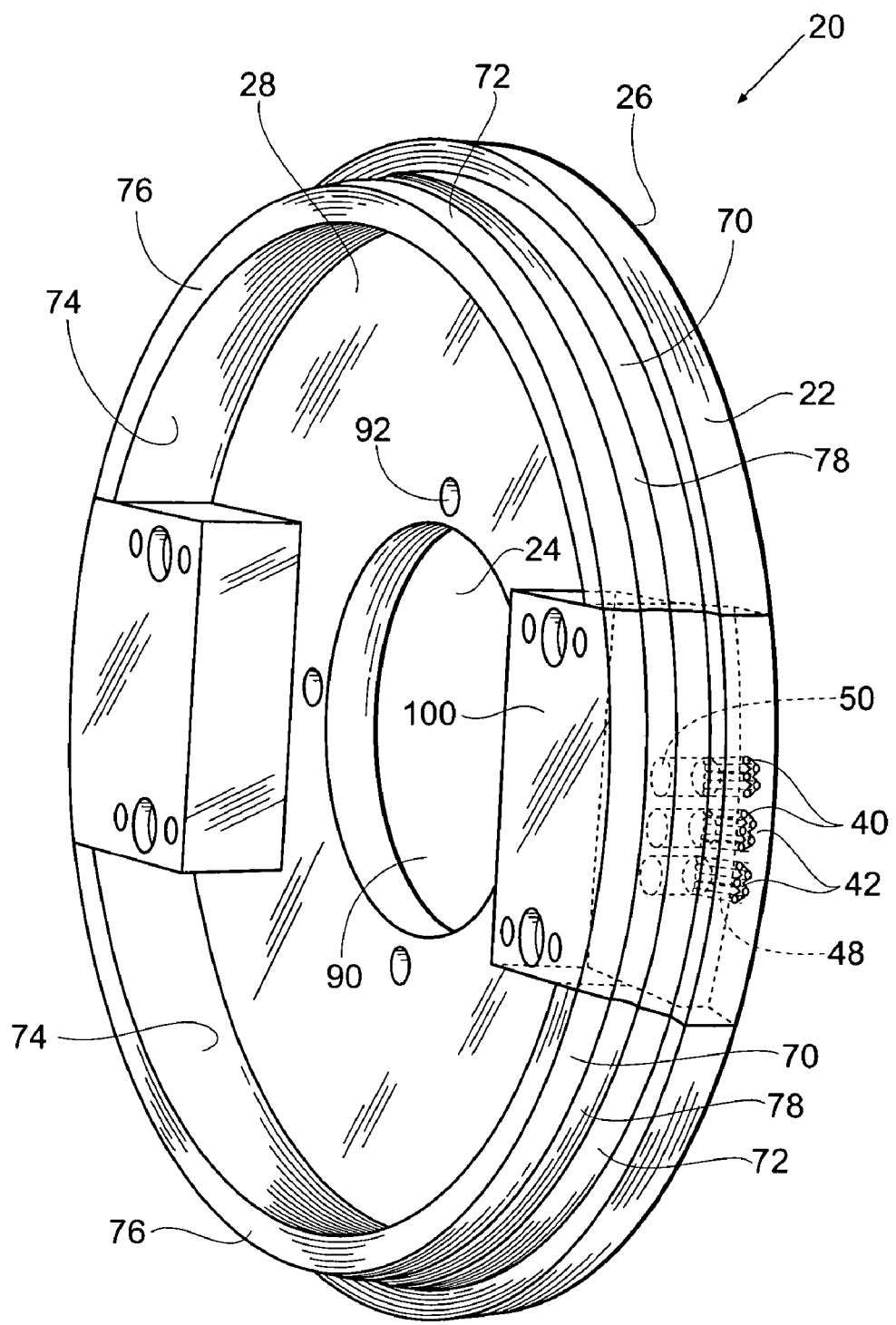
FIG. 8 is a perspective view of a vacuum wheel incorporating inserts.

Referring now to FIG. 8 is a perspective view of the vacuum wheel 20 is shown incorporating inserts 100. The 4 mounting holes 94 (shown in FIG. 6) per grouping of 15 vacuum holes are for the mounting of insert 100.

When mounted to the wheel 20, the inserts 100 complete the protuberance ring. The inserts 100 provide the ability to provide different contact (or gripping) surfaces/methods depending on the type of elastic material being processed. The inserts 100 can be configured for a belt method or for a pad method. A pad method might provide a sandpaper surface, a silicone rubber surface, a surface with pins protruding, etc.

In a preferred embodiment, the "W" pattern shown for example in FIG. 1, can be reversed 180°. In this preferred embodiment, the stretch film tugs against a greater number of points, which has been found to increase the holding effectiveness of the wheel 20.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A vacuum wheel, comprising:
   a rotary member having an perimeter surface, a first side surface and a second side surface;
   a vacuum port for receiving negative pressure provided on the rotary member;
   a vacuum passageway coupled to the vacuum port, said passageway communicating said negative pressure to a plurality of openings disposed in a substantially chevron shaped pattern on said perimeter surface;
   a protuberance further comprising a grooved ring about a periphery of said protuberance.

2. A vacuum wheel, comprising:
   a rotary member having an perimeter surface, a first side surface and a second side surface;
   a vacuum port for receiving negative pressure provided on the rotary member;
   a vacuum passageway coupled to the vacuum port, said passageway communicating said negative pressure to a plurality of openings disposed in a substantially chevron shaped pattern on said perimeter surface;
   the rotary member further comprising a semi-circular protuberance extending from a first side surface of said rotary member,
   a removable insert extending from said first side surface of said rotary member,
   said removable insert having a semi-circular perimeter surface;
   said protuberance and said removable insert extending about a radius of said rotary member, thereby forming a second perimeter surface of said rotary member.

3. A vacuum wheel, comprising:
   a rotary member having an perimeter surface, a first side surface and a second side surface;
   a vacuum port for receiving negative pressure provided on the rotary member;
   a vacuum passageway coupled to the vacuum port, said passageway communicating said negative pressure to a plurality of openings disposed in a substantially chevron shaped pattern on said perimeter surface;
   the rotary member further comprising:
   a plurality of protuberances extending from the rotary member,
   a plurality of removable inserts extending from the rotary member,
   said protuberances and said removable inserts forming a grooved ring about a radius of said member.

4. A vacuum wheel, comprising:
   a rotary member having an perimeter surface, a first side surface and a second side surface;
   a vacuum port for receiving negative pressure provided on the rotary member;
   a vacuum passageway coupled to the vacuum port, said passageway communicating said negative pressure to a plurality of openings disposed in a substantially chevron shaped pattern on said perimeter surface;
   the rotary member further comprising;
   a plurality of protuberances from the rotary member, said protuberances semi-circular about a periphery of said protuberances,
   a plurality of removable inserts extending from the rotary member, said inserts semi-circular about a periphery of said inserts,
   said protuberances and said removable inserts forming a grooved ring about a radius of said member.

* * * * *